(12) United States Patent
Woolard et al.

(10) Patent No.: US 9,872,492 B2
(45) Date of Patent: *Jan. 23, 2018

(54) (S)-ABSCISIC ACID DERIVATIVES FOR THINNING

(71) Applicant: Valent BioSciences Corporation, Libertyville, IL (US)

(72) Inventors: Derek D. Woolard, Zion, IL (US); Gary T. Wang, Libertyville, IL (US); Daniel C. Leep, Lindenhurst, IL (US); Gregory D. Venburg, Deerfield, IL (US)

(73) Assignee: Valent Biosciences LLC, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,808

(22) Filed: May 19, 2016

(65) Prior Publication Data

US 2016/0338352 A1 Nov. 24, 2016

Related U.S. Application Data

(60) Provisional application No. 62/163,615, filed on May 19, 2015.

(51) Int. Cl.
*A01N 43/90* (2006.01)
*A01N 37/42* (2006.01)

(52) U.S. Cl.
CPC .................... *A01N 37/42* (2013.01)

(58) Field of Classification Search
None
See application file for complete search history.

(56) References Cited

U.S. PATENT DOCUMENTS

| 6,004,905 | A | * | 12/1999 | Abrams | A01N 49/00 504/193 |
| 8,173,577 | B2 | * | 5/2012 | Woolard | A01N 37/42 504/116.1 |
| 8,440,592 | B2 | * | 5/2013 | Woolard | A01N 37/42 504/116.1 |
| 8,557,736 | B2 | * | 10/2013 | Woolard | A01N 37/42 504/162 |
| 9,326,508 | B2 | * | 5/2016 | Wang | A01N 37/06 |
| 2008/0227644 | A1 | * | 9/2008 | Woolard | A01N 37/42 504/321 |
| 2008/0254984 | A1 | * | 10/2008 | Woolard | A01N 37/42 504/136 |
| 2010/0317529 | A1 | | 12/2010 | Silverman et al. | |
| 2014/0087949 | A1 | | 3/2014 | Frackenpohl et al. | |

FOREIGN PATENT DOCUMENTS

WO WO1994/015467 7/1994

OTHER PUBLICATIONS

Ueno et al. (Bioorganic and Medicinal Chemistry, 2005, 13(10), 3359-3370).*
International Search Report and Written Opinion dated Sep. 2, 2016 in corresponding PCT Application No. PCT/US2016/033171.

* cited by examiner

*Primary Examiner* — Mina Haghighatian
*Assistant Examiner* — Erin Hirt
(74) *Attorney, Agent, or Firm* — Wood, Phillips, Katz, Clark & Mortimer

(57) ABSTRACT

The present invention is directed to the treatment of apple trees, peach trees, and grape vines with 3'-methyl-(S)-abscisic acid, 3'-propargyl-(S)-abscisic acid, and/or salts thereof in order to reduce the number of fruits on the trees or vines that grow to maturity.

14 Claims, No Drawings

(S)-ABSCISIC ACID DERIVATIVES FOR THINNING

FIELD OF THE INVENTION

The present invention is directed to methods for thinning apple and peach trees and grape vines comprising applying (S)-abscisic acid derivatives to the trees or vines.

BACKGROUND OF THE INVENTION

Many plants, including apple and peach trees and grape vines, naturally set more fruits than is desirable for commercial fruit production. A high fruit crop load can stress the plants which increases their susceptibility to cold injury and disease. Further, having high fruit crop load (set) can cause the plants to only produce fruit every other year, known as biennial bearing.

In addition, the natural high set rates of these plants lead to small fruits which are not as marketable as large fruits. Also high fruit sets may negatively impact the color, sugars, and flavors of the fruits. High fruit sets can also contribute to lower tolerances to storage conditions.

Growers overcome this issue by thinning the fruits which allows the plants to devote their resources to the remaining fruit, thereby producing healthier, larger sized fruits. Thinning can be done by hand or by chemical treatments.

Hand thinning is very resource intensive as it requires someone to remove each undesired fruitlet from the plant. This often requires a lot of time and in the case of trees, the fruitlets may be difficult to reach. Accordingly, hand thinning is very expensive for fruit growers.

Chemical treatments have been used to thin apples, peaches, and grapes. Current commercially available active ingredients used for apple thinning include 1-naphthyl methylcarbamate (Sevin® available from and a registered trademark of Bayer), 6-benzyladenine (MaxCel® available from and a registered trademark of Valent BioSciences Corporation), and 6-benzyladenine with gibberellin 4/7 (Promalin® available from and a registered trademark of Valent BioSciences Corporation). However, each of these commercially available products has their drawbacks. For example, 1-naphthyl methylcarbamate (Sevin®) is a very effective thinner, but it has significant ecotoxicity and bee toxicity. Sevin® has been banned as a thinning agent in Europe. MaxCel® is not as robust of a thinner as Sevin®, but it increases fruit size. Promalin® has some thinning effect, but it is most useful as a fruit shape modification product.

Currently, there is not a commercially available chemical thinner for peach trees. Growers have tried numerous chemical treatments but the results are not consistent or negative side effects make them unusable.

The chemical treatment standard for thinning seedless grapes is gibberellic acid. However, gibberellic acid treatments may cause reduced bloom density in the following year, especially on seeded grapes.

(S)-abscisic acid ("S-ABA") can thin fruits; however, the effective rates are cost prohibitive.

Accordingly, there is a need for new methods for thinning apple trees, peach trees, and grape vines to produce highly marketable fruits. The new methods should be cost-effective for the growers and produce consistent and reliable thinning results.

SUMMARY OF THE INVENTION

The present invention is directed to methods for thinning apple and peach trees and grape vines comprising applying 3'-methyl-(S)-abscisic acid, 3'-propargyl-(S)-abscisic acid, and salts thereof to the trees or vines.

DETAILED DESCRIPTION OF THE INVENTION

Recently, Applicant discovered new S-ABA derivatives (see U.S. Patent Application No. 62/022,037 and Ser. No. 14/593,597). Applicant determined that two derivatives were unexpectedly more potent than S-ABA. Specifically, these derivatives are (2Z,4E)-5-((S)-1-hydroxy-2,3,6,6-tetramethyl-4-oxocyclohex-2-en-1-yl)-3-methylpenta-2,4-dienoic acid ("3'-methyl-(S)-abscisic acid") and (2Z,4E)-5-((S)-1-hydroxy-2,6,6-trimethyl-4-oxo-3-(prop-2-yn-1-yl)cyclohex-2-en-1-yl)-3-methylpenta-2,4-dienoic acid ("3'-propargyl-(S)-abscisic acid"). The structures of these derivatives are below:

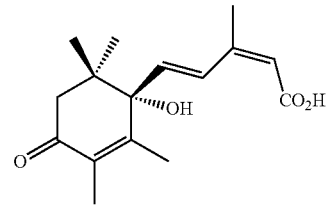

3'-methyl-(S)-abscisic acid

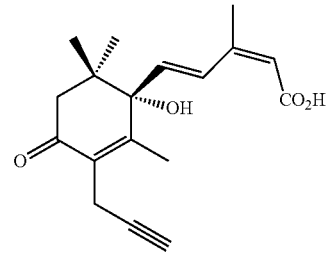

3'-propargyl-(S)-abscisic acid

Applicant unexpectedly found that the abscisic acid derivatives 3'-methyl-(S)-abscisic acid and 3'-propargyl-(S)-abscisic acid provided excellent thinning of apple trees while maintaining high fruit yields. For example, Applicant unexpectedly discovered that addition of 3'-methyl-(S)-ABA to 6-benzyladenine treatments increased thinning of apple trees. Further, Applicant unexpectedly discovered 3'-methyl-(S)-ABA was a more potent thinner than S-ABA when used in combination with 6-benzyladenine.

Thinning of Apple Trees

In one embodiment, the present invention is directed to methods for thinning an apple tree comprising applying an abscisic acid derivative selected from the group consisting of 3'-methyl-(S)-abscisic acid, 3'-propargyl-(S)-abscisic acid, and salts thereof to the apple tree.

In a preferred embodiment, the abscisic acid derivative applied to the apple tree is 3'-methyl-(S)-abscisic acid.

In another embodiment, the 3'-methyl-(S)-abscisic acid is applied to the apple tree at a rate of from about 10 to about 150 grams per acre. In a preferred embodiment, the 3'-methyl-(S)-abscisic acid is applied to the apple tree at a rate of from about 35 to about 125 grams per acre. In a more preferred embodiment, the 3'-methyl-(S)-abscisic acid is applied to the apple tree at a rate of from about 50 to about 115 grams per acre.

In a further embodiment, the 3'-methyl-(S)-abscisic acid is applied to the apple tree during the period beginning when the fruit is about 5 mm in diameter and ending when the fruit is more than 15 mm in diameter. In a preferred embodiment, the 3'-methyl-(S)-abscisic acid is applied to the apple tree during the period beginning when the fruit is about 7 mm in diameter and ending when the fruit is about 14 mm in diameter. In a more preferred embodiment, the 3'-methyl-(S)-abscisic acid is applied to the apple tree during the period beginning when the fruit is about 8 mm in diameter and ending when the fruit is about 13 mm in diameter. In a most preferred embodiment, the 3'-methyl-(S)-abscisic acid is applied to the apple tree during the period beginning when the fruit is about 8 mm in diameter and ending when the fruit is about 12 mm in diameter.

In another embodiment, the 3'-methyl-(S)-abscisic acid is applied to an apple tree selected from the group consisting of Idared, Braeburn, Cameo, Cortland, crabapple, Empire, Fuji, Gala, Ginger Gold, Golden Delicious, Granny Smith, Honeycrisp, Jonagold, Jonathan, McIntosh, Mutsu, Nittany, Pink Lady, Rome, Red Delicious, Stayman, Winesap, and York. In a preferred embodiment, the apples are Gala or McIntosh.

In a further embodiment, the 3'-methyl-(S)-abscisic acid is applied to the apple tree with another plant growth regulator. In a preferred embodiment, the plant growth regulator is selected from the group consisting of cytokinins, gibberellins, auxins, organic acids, and ethylene precursors. In a more preferred embodiment, the plant growth regulator is a cytokinin. In a most preferred embodiment, the cytokinin is 6-benzyladenine.

In another embodiment, the amount of cytokinin that is applied is from about 15 to about 45 grams per acre. In a preferred embodiment, the amount of cytokinin that is applied is from about 20 to about 40 grams per acre. In a more preferred embodiment, the amount of cytokinin that is applied is from about 25 to about 30 grams per acre.

In another preferred embodiment, the ethylene precursor is ethephon or 1-aminocyclopropane carboxylic acid.

In an alternative preferred embodiment, the abscisic acid derivative applied to the apple tree is 3'-propargyl-(S)-abscisic acid.

In another embodiment, the 3'-propargyl-(S)-abscisic acid is applied to the apple tree at a rate of from about 10 to about 150 grams per acre. In a preferred embodiment, the 3'-propargyl-(S)-abscisic acid is applied to the apple tree at a rate of from about 35 to about 125 grams per acre. In a more preferred embodiment, the 3'-propargyl-(S)-abscisic acid is applied to the apple tree at a rate of from about 50 to about 115 grams per acre.

In a further embodiment, the 3'-propargyl-(S)-abscisic acid is applied to the apple tree during the period beginning when the fruit is about 5 mm in diameter and ending when the fruit is more than 15 mm in diameter. In a preferred embodiment, the 3'-propargyl-(S)-abscisic acid is applied to the tree during the period beginning when the fruit is about 7 mm in diameter and ending when the fruit is about 14 mm in diameter. In a more preferred embodiment, the 3'-propargyl-(S)-abscisic acid is applied to the apple tree during the period beginning when the fruit is about 8 mm in diameter and ending when the fruit is about 13 mm in diameter. In a most preferred embodiment, the 3'-propargyl-(S)-abscisic acid is applied to the apple tree during the period beginning when the fruit is about 8 mm in diameter and ending when the fruit is about 12 mm in diameter.

In another embodiment, the 3'-propargyl-(S)-abscisic acid is applied to an apple tree selected from the group consisting of Idared, Braeburn, Cameo, Cortland, crabapple, Empire, Fuji, Gala, Ginger Gold, Golden Delicious, Granny Smith, Honeycrisp, Jonagold, Jonathan, McIntosh, Mutsu, Nittany, Pink Lady, Rome, Red Delicious, Stayman, Winesap and York. In a preferred embodiment, the apples are Gala or McIntosh.

In a further embodiment, the 3'-propargyl-(S)-abscisic acid is applied with another plant growth regulator to the apple tree. In a preferred embodiment, the plant growth regulator is selected from the group consisting of cytokinins, gibberellins, auxins, organic acids, and ethylene precursors. In a more preferred embodiment, the plant growth regulator is a cytokinin. In a most preferred embodiment, the cytokinin is 6-benzyladenine.

In another embodiment, the amount of cytokinin that is applied is from about 15 to about 45 grams per acre. In a preferred embodiment, the amount of cytokinin that is applied is from about 20 to about 40 grams per acre. In a more preferred embodiment, the amount of cytokinin that is applied is from about 25 to about 30 grams per acre.

In another preferred embodiment, the ethylene precursor is ethephon or 1-aminocyclopropane carboxylic acid.

Thinning of Peach Trees

In one embodiment, the present invention is directed to methods for thinning a peach tree comprising applying an abscisic acid derivative selected from the group consisting of 3'-methyl-(S)-abscisic acid, 3'-propargyl-(S)-abscisic acid, and salts thereof to the peach tree.

In a preferred embodiment, the abscisic acid derivative applied to the peach tree is 3'-methyl-(S)-abscisic acid.

In another embodiment, the 3'-methyl-(S)-abscisic acid is applied to the peach tree at a rate of from about 10 to about 150 grams per acre. In a preferred embodiment, the 3'-methyl-(S)-abscisic acid is applied to the peach tree at a rate of from about 35 to about 125 grams per acre. In a more preferred embodiment, the 3'-methyl-(S)-abscisic acid is applied to the peach tree at a rate of from about 50 to about 115 grams per acre.

In a further embodiment, the 3'-methyl-(S)-abscisic acid is applied to the peach tree during the period beginning when the fruit is about 5 mm in diameter and ending when the fruit is more than 15 mm in diameter. In a preferred embodiment, the 3'-methyl-(S)-abscisic acid is applied to the peach tree during the period beginning when the fruit is about 7 mm in diameter and ending when the fruit is about 14 mm in diameter. In a more preferred embodiment, the 3'-methyl-(S)-abscisic acid is applied to the peach tree during the period beginning when the fruit is about 8 mm in diameter and ending when the fruit is about 13 mm in diameter. In a most preferred embodiment, the 3'-methyl-(S)-abscisic acid is applied to the peach tree during the period beginning when the fruit is about 8 mm in diameter and ending when the fruit is about 12 mm in diameter.

In another embodiment, the 3'-methyl-(S)-abscisic acid is applied to a peach tree selected from the group consisting of Autumn Flame, Babygold #5, Elegant Lady, Encore, Goldprince, Goldnine, Harvester, O'Henry, PF-27, Redglobe, Redhaven, Rich Lady, and September Sun.

In a further embodiment, the 3'-methyl-(S)-abscisic acid is applied to the peach tree with another plant growth regulator. In a preferred embodiment, the plant growth regulator is selected from the group consisting of cytokinins, gibberellins, auxins, organic acids, and ethylene precursors. In a more preferred embodiment, the plant growth regulator is a cytokinin. In a most preferred embodiment, the cytokinin is 6-benzyladenine.

In another embodiment, the amount of cytokinin that is applied is from about 15 to about 45 grams per acre. In a preferred embodiment, the amount of cytokinin that is applied is from about 20 to about 40 grams per acre. In a more preferred embodiment, the amount of cytokinin that is applied is from about 25 to about 30 grams per acre.

In an alternative preferred embodiment, the abscisic acid derivative applied to the peach tree is 3'-propargyl-(S)-abscisic acid.

In another embodiment, the 3'-propargyl-(S)-abscisic acid is applied to the peach tree at a rate of from about 10 to about 150 grams per acre. In a preferred embodiment, the 3'-propargyl-(S)-abscisic acid is applied to the peach tree at a rate of from about 35 to about 125 grams per acre. In a more preferred embodiment, the 3'-propargyl-(S)-abscisic acid is applied to the peach tree at a rate of from about 50 to about 115 grams per acre.

In a further embodiment, the 3'-propargyl-(S)-abscisic acid is applied to the peach tree during the period beginning when the fruit is about 5 mm in diameter and ending when the fruit is more than 15 mm in diameter. In a preferred embodiment, the 3'-propargyl-(S)-abscisic acid is applied to the peach tree during the period beginning when the fruit is about 7 mm in diameter and ending when the fruit is about 14 mm in diameter. In a more preferred embodiment, the 3'-propargyl-(S)-abscisic acid is applied to the peach tree during the period beginning when the fruit is about 8 mm in diameter and ending when the fruit is about 13 mm in diameter. In a most preferred embodiment, the 3'-propargyl-(S)-abscisic acid is applied to the peach tree during the period beginning when the fruit is about 8 mm in diameter and ending when the fruit is about 12 mm in diameter.

In another embodiment, the 3'-propargyl-(S)-abscisic acid is applied to a peach tree selected from the group consisting of Autumn Flame, Babygold #5, Elegant Lady, Encore, Goldprince, Goldnine, Harvester, O'Henry, PF-27, Redglobe, Redhaven, Rich Lady and September Sun.

In a further embodiment, the 3'-propargyl-(S)-abscisic acid is applied with another plant growth regulator to the peach tree. In a preferred embodiment, the plant growth regulator is selected from the group consisting of cytokinins, gibberellins, auxins, organic acids, and ethylene precursors. In a more preferred embodiment, the plant growth regulator is a cytokinin. In a most preferred embodiment, the cytokinin is 6-benzyladenine.

In another embodiment, the amount of cytokinin that is applied is from about 15 to about 45 grams per acre. In a preferred embodiment, the amount of cytokinin that is applied is from about 20 to about 40 grams per acre. In a more preferred embodiment, the amount of cytokinin that is applied is from about 25 to about 30 grams per acre.

In another preferred embodiment, the ethylene precursor is ethephon or 1-aminocyclopropane carboxylic acid.

Thinning of Grape Vines

In an embodiment, the present invention is directed to methods for thinning a grape vine comprising applying an abscisic acid derivative selected from the group consisting of 3'-methyl-(S)-abscisic acid, 3'-propargyl-(S)-abscisic acid, and salts thereof to the grape vine.

In a preferred embodiment, the abscisic acid derivative applied to the grape vine is 3'-methyl-(S)-abscisic acid.

In another embodiment, the 3'-methyl-(S)-abscisic acid is applied to the grape vines at a rate of from about 10 to about 150 grams per acre. In a preferred embodiment, the 3'-methyl-(S)-abscisic acid is applied to the grape vines at a rate of from about 35 to about 125 grams per acre. In a more preferred embodiment, the 3'-methyl-(S)-abscisic acid is applied to the grape vines at a rate of from about 50 to about 115 grams per acre.

In a further embodiment, the 3'-methyl-(S)-abscisic acid is applied to the grape vine during the period beginning when the cluster begins to bloom and ending when the fruit is more than 5 mm in diameter. In a preferred embodiment, the 3'-methyl-(S)-abscisic acid is applied to the vine during the period beginning when the cluster begins to bloom and ending when the fruit is about 3 mm in diameter. In a most preferred embodiment, the 3'-methyl-(S)-abscisic acid is applied to the grape vine during the period beginning when the cluster begins to bloom and ending when the fruit is about 1 mm in diameter. Repeated applications may be beneficial.

In another embodiment, the 3'-methyl-(S)-abscisic acid is applied to a grape vine selected from the group consisting of Autumn Royal, Cabernet Franc, Cabernet Sauvignon, Chardonnay, Crimson Seedless, Flame Seedless, Grenache, Merlot, Syrah, Pinot Noir, Zinfandel, Chenin Blanc, Muscat, Pinot Grigio, Red Globe, Sauvignon Blanc, Sugraone, Superior Seedless and Thompson Seedless. In a preferred embodiment, the grape vine is Superior Seedless.

In a further embodiment, the 3'-methyl-(S)-abscisic acid is applied to the grape vine with another plant growth regulator. In a preferred embodiment, the plant growth regulator is selected from the group consisting of cytokinins, gibberellins, auxins, organic acids, and ethylene precursors. In a more preferred embodiment, the plant growth regulator is a cytokinin. In a most preferred embodiment, the cytokinin is 6-benzyladenine. In another embodiment, the amount of cytokinin that is applied is from about 15 to about 45 grams per acre. In a preferred embodiment, the amount of cytokinin that is applied is from about 20 to about 40 grams per acre. In a more preferred embodiment, the amount of cytokinin that is applied is from about 25 to about 30 grams per acre.

In another preferred embodiment, the ethylene precursor is ethephon or 1-aminocyclopropane carboxylic acid.

In an alternative preferred embodiment, the abscisic acid derivative applied to the grape vine is 3'-propargyl-(S)-abscisic acid.

In another embodiment, the 3'-propargyl-(S)-abscisic acid is applied to the grape vines at a rate of from about 10 to about 150 grams per acre. In a preferred embodiment, the 3'-propargyl-(S)-abscisic acid is applied to the grape vines at a rate of from about 35 to about 125 grams per acre. In a more preferred embodiment, the 3'-propargyl-(S)-abscisic acid is applied to the grape vines at a rate of from about 50 to about 115 grams per acre.

In a further embodiment, the 3'-propargyl-(S)-abscisic acid is applied to the grape vine during the period beginning when the cluster begins to bloom and ending when the fruit is more than 5 mm in diameter. In a preferred embodiment, the 3'-propargyl-(S)-abscisic acid is applied to the vine during the period beginning when the cluster begins to bloom and ending when the fruit is about 3 mm in diameter. In a most preferred embodiment, the 3'-propargyl-(S)-abscisic acid is applied to the grape vine during the period beginning when the cluster begins to bloom and ending when the fruit is about 1 mm in diameter. Repeat applications may be beneficial.

In another embodiment, the 3'-propargyl-(S)-abscisic acid is applied to a grape vine selected from the group consisting, but not limited to Autumn Royal, Cabernet Franc, Cabernet Sauvignon, Chardonnay, Crimson Seedless, Flame Seedless, Grenache, Merlot, Syrah, Pinot Noir, Zinfandel, Chenin Blanc, Muscat, Pinot Grigio, Red Globe, Sauvignon Blanc, Sugraone, Superior Seedless and Thompson Seedless. In a preferred embodiment, the grapes are Superior Seedless.

In a further embodiment, the 3'-propargyl-(S)-abscisic acid is applied with another plant growth regulator to the grape vine. In a preferred embodiment, the plant growth regulator is selected from the group consisting of cytokinins, gibberellins, auxins, organic acids, and ethylene precursors. In a more preferred embodiment, the plant growth regulator is a cytokinin. In a most preferred embodiment, the cytokinin is 6-benzyladenine. In another embodiment, the amount of cytokinin that is applied is from about 15 to about 45 grams per acre. In a preferred embodiment, the amount of cytokinin that is applied is from about 20 to about 40 grams per acre. In a more preferred embodiment, the amount of cytokinin that is applied is from about 25 to about 30 grams per acre.

In another preferred embodiment, the ethylene precursor is ethephon or 1-aminocyclopropane carboxylic acid.

The abscisic acid derivatives claimed herein are enantiomerically pure "(S)" derivatives, meaning that "(2Z,4E)-5-((S)-1-hydroxy-2,3,6,6-tetramethyl-4-oxocyclohex-2-en-1-yl)-3-methylpenta-2,4-dienoic acid," "(2Z,4E)-5-((S)-1-hydroxy-2,6,6-trimethyl-4-oxo-3-(prop-2-yn-1-yl) cyclohex-2-en-1-yl)-3-methylpenta-2,4-dienoic acid," "3'-propargyl-(S)-abscisic acid," and "3'-methyl-(S)-abscisic acid" refer to derivatives comprising greater than 95% purity of the "(S)" enantiomer. This means that the compounds claimed herein are not "racemic" or "(±)." "Racemic" and "(±)" refer to derivatives with a relatively equal mixture of R/S enantiomers.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases. Suitable salts include inorganic salts such as the ammonium, lithium, sodium, potassium, magnesium and calcium salts and organic amine salts such as the triethanolamine, dimethylethanolamine and ethanolamine salts.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise.

The following examples are intended to illustrate the present invention and to teach one of ordinary skill in the art how to use the formulations of the invention. They are not intended to be limiting in any way.

EXAMPLES

Example 1. Thinning Study of McIntosh Apple

In a study carried out in Michigan, 3'-methyl-(S)-abscisic acid was mixed with 6-benzyladenine and compared with a mixture of S-ABA and 6-benzyladenine. 3'-Methyl-(S)-abscisic acid was formulated as a potassium salt in an aqueous. S-ABA was formulated as potassium salt in an aqueous formulation. MaxCel®, a 2% (w/w) 6-benzyladenine formulation, was used as the source of 6-benzyladenine ("6-BA" in the following tables).

The treatments were applied to McIntosh apple in fields when the fruit reached 10 mm in size. Six single tree replicates were sprayed with the equivalent of 100 gallons per acre using a motorized backpack mist blower. All the trees in the study were matched to about the same size and initial cropload. The fruit was harvested at maturity and the average fruit weights for each treatment group were recorded. The results are shown in Table 1 (the lower the number of fruits, the greater the thinning effect of the treatment).

TABLE 1

Effect of S-ABA and 3'-methyl-(S)-ABA on Thinning McIntosh Apples

| Treatment | Average Number of Fruit per Tree | Average Fruit Weight (gram) |
|---|---|---|
| Untreated | 175 | 91 |
| 6-BA (28 g/acre) | 130 | 94 |
| 3'-methyl-(S)-ABA (11.35 g/acre, 30 ppm) + 6-BA (28 g/acre) | 133 | 94 |
| 3'-methyl-(S)-ABA (37.85 g/acre, 100 ppm) + 6-BA (28 g/acre) | 118 | 95 |
| 3'-methyl-(S)-ABA (113.5 g/acre, 300 ppm) + 6-BA (28 g/acre) | 105 | 97 |
| S-ABA (113.5 g/acre, 300 ppm) + 6-BA (28 g/acre) | 126 | 97 |
| S-ABA (378.5 g/acre, 1000 ppm) + 6-BA (28 g/acre) | 119 | 100 |

The data in Table 1 show that McIntosh apple trees that were not thinned retained an average of 175 fruit per tree. Treating trees with 6-benzyladenine thinned the number of fruit to an average of 130 fruit per tree. Applicant unexpectedly discovered that addition of 3'-methyl-(S)-ABA to the 6-benzyladenine solution increased thinning of McIntosh apple in a dose-dependent manner and that 3'-methyl-(S)-ABA was a more potent thinner than S-ABA when used in combination with 6-benzyladenine. Thus, addition of 100 ppm 3'-methyl-(S)-ABA (37.85 g/acre) to 6-benzyladenine (28 g/acre) reduced crop load to 118 fruit/tree, essentially the same as the fruit load of 119 with 1000 ppm S-ABA (378.5 g/acre) plus 6-benzyladenine (28 g/acre), suggesting that the S-ABA derivative is about 10 times as potent as S-ABA. One of the benefits of fruit thinning is bigger fruit, as measured by average fruit weights. The data in Table 1 confirmed that stronger thinning effects (lower fruit set) resulted in bigger fruits.

Example 2. Thinning Study of Gala Apple (Michigan)

A further study was carried out in Michigan, following the same protocol as described in Example 1. The results are summarized in Table 2.

TABLE 2

Effect of Thinning on Apples

| Treatment | Average Number of Fruit per Tree | Average fruit weight (gram) |
|---|---|---|
| Untreated | 224 | 91 |
| 6-BA (28 g/acre, 75 ppm) | 249 | 90 |

TABLE 2-continued

Effect of Thinning on Apples

| Treatment | Average Number of Fruit per Tree | Average fruit weight (gram) |
|---|---|---|
| 3'-methyl-(S)-ABA (11.35 g/acre, 30 ppm) + 6-BA (28 g/acre, 75 ppm) | 251 | 92 |
| 3'-methyl-(S)-ABA (37.85 g/acre, 100 ppm) + 6-BA (28 g/acre, 75 ppm) | 230 | 94 |
| 3'-methyl-(S)-ABA (113.5 g/acre, 300 ppm) + 6-BA (28 g/acre, 75 ppm) | 156 | 106 |
| S-ABA (113.5 g/acre, 300 ppm) + 6-BA (28 g/acre, 75 ppm | 204 | 101 |
| S-ABA (378.5 g/acre, 1000 ppm) + 6-BA (28 g/acre, 75 ppm) | 153 | 112 |

Gala apple trees that were not thinned retained an average of 224 fruit per tree. Treating trees with 6-benzyladenine alone did not reduce crop load (thinning) and the trees averaged 249 fruit per tree. Applicant unexpectedly discovered that addition of 3'-methyl-(S)-ABA to the 6-benzyladenine solution increased thinning of Gala apple in a dose dependent manner and that 3'-methyl-(S)-ABA was a more potent thinner than S-ABA when used in combination with 6-benzyladenine. Thus, addition of 300 ppm 3'-methyl-(S)-ABA (113.5 g/acre) to 6-benzyladenine (28 g/acre) reduced the fruit load to 156, considerably lower than the fruit load of 204 with 300 ppm S-ABA (113.5 g/acre) plus 6-benzyladenine (28 g/acre) and compares favorably with the fruit load of 122 for the 1000 ppm S-ABA (378.5 g/acre) and 6-benzyladenine (28 g/acre) combination. This data suggests that the S-ABA derivative is more potent than S-ABA. The average fruit weight data in Table 2 was consistent with the thinning data. Thus, Gala apples from trees treated with 300 ppm 3'-methyl-(S)-ABA (113.5 g/acre) plus 6-benzyladenine (28 g/acre) averaged 106 grams per apple, in contrast with 91 grams and 90 grams for Gala apples from untreated trees and trees treated with 6-benzyladenine (75 ppm, 28 g/acre) alone, respectively.

Example 3. Thinning Study of Gala Apple (Michigan)

The thinning study of Gala apple was repeated in Gala in Michigan following the same protocol described in Example 1. In addition to S-ABA and 3'methyl-(S)-ABA, 3'-propargyl-(S)-ABA was also tested for this effect. The results are summarized in Table 3.

TABLE 3

Effect of Thinning on Apples

| Treatment | Average Number of Fruit per Tree | Average Fruit Weight (gram) |
|---|---|---|
| Untreated | 237 | 123 |
| 3'-methyl-(S)-ABA (11.35 g/acre, 30 ppm) + 6-BA (28 g/acre, 75 ppm) | 155 | 144 |
| 3'-methyl-(S)-ABA (37.85 g/acre, 100 ppm) + 6-BA (28 g/acre, 75 ppm) | 142 | 134 |
| 3'-methyl-(S)-ABA (113.5 g/acre, 300 ppm) + 6-BA (28 g/acre, 75 ppm) | 122 | 147 |
| 3'-propargyl-(S)-ABA (113.5 g/acre, 300 ppm) + 6-BA (28 g/acre, 75 ppm) | 133 | 142 |
| S-ABA (113.5 g/acre, 300 ppm) + 6-BA (28 g/acre, 75 ppm) | 147 | 145 |

TABLE 3-continued

Effect of Thinning on Apples

| Treatment | Average Number of Fruit per Tree | Average Fruit Weight (gram) |
|---|---|---|
| S-ABA (378.5 g/acre, 1000 ppm) + 6-BA (28 g/acre, 75 ppm) | 112 | 148 |

Consistent with the results from the study in Example 1, Applicant discovered that addition of 3'-methyl-(S)-ABA to the 6-benzyladenine treatment increased thinning of Gala apple in a dose dependent manner. Quantitatively, a combination of 100 ppm 3'-methyl-(S)-ABA (37.85 g/acre) and 6-benzyladenine (28 g/acre) reduced fruit load to 142, compared to a fruit load of 237 for untreated trees and 147 for trees treated with a combination of 300 ppm S-ABA (113.5 g/acre) and 6-benzyladenine (28 g/acre), suggesting that 3'-methyl-(S)-ABA is about three times more potent than S-ABA. Applicant discovered that 3'-propargyl-(S)-ABA, in combination with 6-benzyladenine, also caused significant thinning of Gala apple. The combination of 300 ppm 3'-propargyl-(S)-ABA (113.5 g/acre) and 6-benzyladenine (28 g/acre) reduced fruit load to 133, compared to a fruit load of 237 for untreated trees and 147 for trees treated with a combination of 300 ppm S-ABA (113.5 g/acre) and 6-benzyladenine (28 g/acre).

Example 4. Thinning Study of Gala Apple (Washington)

Another thinning study of Gala apple was carried out in Washington using a procedure of chemical thinning followed by hand thinning. For chemical thinning, trees (size matched across all the treatment groups) were sprayed with 6-benzyladenine combined with S-ABA or S-ABA derivatives at about the 10 mm fruit diameter timing, as described in Example 1. After a period known as "June drop," the trees were further thinned by hand to achieve the essentially identical fruit load that was deemed to be the appropriate crop load. This practice will ensure a uni-size apple crop. With this protocol, a lower requirement for the number of fruits removed by hand indicates a more efficacious chemical thinning treatment. The results are summarized in Table 4.

TABLE 4

Effect of Thinning on Apples

| Treatment | Hand Thinned Fruit per Tree |
|---|---|
| Untreated | 66.8 |
| 3'-methyl-(S)-ABA (11.35 g/acre, 30 ppm) + 6-BA (28 g/acre, 75 ppm) | 57.8 |
| 3'-methyl-(S)-ABA (37.85 g/acre, 100 ppm) + 6-BA (28 g/acre, 75 ppm) | 30.0 |
| 3'-methyl-(S)-ABA (113.5 g/acre, 300 ppm) + 6-BA (28 g/acre, 75 ppm) | 15.6 |
| 3'-propargyl-(S)-ABA (113.5 g/acre, 300 ppm) + 6-BA (28 g/acre, 75 ppm) | 19.6 |
| S-ABA (113.5 g/acre, 300 ppm) + 6-BA (28 g/acre, 75 ppm) | 28.2 |
| S-ABA (378.5 g/acre, 1000 ppm) + 6-BA (28 g/acre, 75 ppm) | 19.2 |

The data in Table 4 provides further support of the results described in Tables 2 and 3. Accordingly, Gala apple trees that were not treated with prior chemical thinning required hand removal of about 67 fruitlets per tree. Addition of S-ABA or S-ABA derivatives to the 6-benzyladenine solution increased thinning in a dose dependent manner so that fewer fruitlets were needed to be removed by hand. Furthermore, a combination of 300 ppm 3'-methyl-ABA (113.5 g/acre) and 6-benzyladenine (28 g/acre) reduced the number of fruit that were hand thinned to 15.5, in comparison with 19.2 when the initial chemical thinning was done with a combination of 1000 ppm S-ABA (378.5 g/acre) and 6-benzyladenine (28 g/acre), suggesting that 3'-methyl-(S)-ABA is about three times more potent than S-ABA. The combination of 300 ppm 3'-propargyl-(S)-ABA (113.5 g/acre) and 6-benzyladenine (28 g/acre) reduced the number of fruit that were hand thinned to 19.6, comparable with the corresponding number for the 1000 ppm S-ABA (378.5 mg/acre) and 6-benzyladenine combination (19.2), suggesting that 3'-propargyl-(S)-ABA is also about three times more potent than S-ABA.

Example 5. Thinning Study on Peach

A study was conducted in Washington (Yakima, Wash.) to determine the effect of S-ABA and 3'-methyl-(S)-abscisic acid on Rich Lady peach thinning.

TABLE 5

Effect of S-ABA and 3'-methyl-(S)-abscisic acid on Rich Lady Peach

| Treatment | Conc. (ppm) | Initial fruit set per cluster | Number hand thinned per tree | Harvest percent fruit 125 ct/box or larger |
|---|---|---|---|---|
| UTC | | 0.69 | 56.4 | 25.4 |
| 3'-methyl-(S)-abscisic acid | 30 | 0.63 | 61.8 | 25.0 |
| 3'-methyl-(S)-abscisic acid | 100 | 0.69 | 59.2 | 30.2 |
| 3'-methyl-(S)-abscisic acid | 300 | 0.56 | 45.4 | 37.6 |
| S-ABA | 300 | 0.64 | 61.2 | 27.6 |
| S-ABA | 1000 | 0.66 | 67.8 | 29.7 |

All treatments contained 0.05% Regulaid surfactant

In this study, the initial fruit set prior to treatment was relatively uniform across the treatment groups with the exception of the 300 ppm 3'-methyl-(S)-abscisic acid treatment that had lower fruit set. Following the treatments and a period of time for fruit to drop, the trees were hand-thinned to achieve a desired commercially optimal fruit load. As seen in Table 5, the number of fruit that had to be hand thinned was slightly reduced as the concentration of 3'-methyl-(S)-abscisic acid increases, indicating that the 3'-methyl-(S)-abscisic acid treatment caused fruit drop (thinning). The fruit size also follows the same pattern in that the fruit size, as indicated by the percent of the fruit in the 125 count/box or larger fruit, increases with higher use rate of 3'-methyl-(S)-abscisic acid. The S-ABA treatments unexpectedly did not reduce the hand thinning required, but did result in small increase in the fruit size in a dose dependent manner.

Another study was conducted to determine the effect of S-ABA and 3'-methyl-(S)-abscisic acid on peach thinning. Unfortunately, the fruits were hand-thinned by the grower after the treatments were applied. Accordingly, the effectiveness of the treatments could not be determined and no data was collected.

Example 7. Thinning Study on Superior Seedless Grape

A grape study was conducted to determine the effect of S-ABA and 3'-methyl-(S)-abscisic acid on flower and/or fruit thinning. S-ABA was applied at 37 to 115 grams/acre rate. 3'-methyl-(S)-abscisic acid was applied at 10 to 115 grams/acre rate.

Unfortunately, the grapes were hand-thinned by the grower after the treatments were applied. Accordingly, the effectiveness of the treatments could not be determined and no data was collected.

The invention claimed is:

1. A method of thinning an apple tree comprising applying from about 100 to about 300 parts per million of an abscisic acid derivative selected from the group consisting of (2Z,4E)-5-((S)-1-hydroxy-2,3,6,6-tetramethyl-4-oxocyclohex-2-en-1-yl)-3-methylpenta-2,4-dienoic acid (3'-methyl-(S)-abscisic acid), (2Z,4E)-5-((S)-1-hydroxy-2,6,6-trimethyl-4-oxo-3-(prop-2-yn-1-yl)cyclohex-2-en-1-yl)-3-methylpenta-2,4-dienoic acid (3'-propargyl-(S)-abscisic acid), and a salt thereof to the apple tree.

2. The method of claim 1 wherein the abscisic acid derivative is 3'-methyl-(S)-abscisic acid.

3. The method of claim 2 wherein 3'-methyl-(S)-abscisic acid is applied at a rate of from about 38 to about 113 grams per acre.

4. The method of claim 2 wherein 3'-methyl-(S)-abscisic acid is applied to the tree during the period beginning when the fruit is about 5 mm in diameter and ending when the fruit is about 15 mm in diameter.

5. The method of claim 2 wherein the apple tree is selected from the group consisting of Idared, Braeburn, Cameo, Cortland, crabapple, Empire, Fuji, Gala, Ginger Gold, Golden Delicious, Granny Smith, Honeycrisp, Jonagold, Jonathan, McIntosh, Mutsu, Nittany, Pink Lady, Rome, Red Delicious, Stayman, Winesap and York.

6. The method of claim 2 wherein the abscisic acid derivative is applied with a plant growth regulator selected from the group consisting of cytokinins, gibberellins, auxins, organic acids, and ethylene precursors.

7. The method of claim 6 wherein the cytokinin is 6-benzyladenine.

8. The method of claim 1 wherein the abscisic acid derivative is 3'-propargyl-(S)-abscisic acid.

9. The method of claim 8 wherein 3'-propargyl-(S)-abscisic acid is applied at a rate of from about 38 to about 113 grams per acre.

10. The method of claim 8 wherein 3'-propargyl-(S)-abscisic acid is applied to the tree during the period beginning when the fruit is about 5 mm in diameter and ending when the fruit is about 15 mm in diameter.

11. The method of claim 8 wherein the apple tree is selected from the group consisting of Idared, Braeburn, Cameo, Cortland, crabapple, Empire, Fuji, Gala, Ginger Gold, Golden Delicious, Granny Smith, Honeycrisp, Jonagold, Jonathan, McIntosh, Mutsu, Nittany, Pink Lady, Rome, Red Delicious, Stayman, Winesap and York.

12. The method of claim 8 wherein 3'-propargyl-(S)-abscisic acid is applied with a plant growth regulator selected from the group consisting of cytokinins, gibberellins, auxins, organic acids, and ethylene precursors.

13. The method of claim 8 wherein the cytokinin is 6-benzyladenine.

14. A method of thinning a peach tree comprising applying from about 100 to about 300 parts per million of (2Z,4E)-5-((S)-1-hydroxy-2,3,6,6-tetramethyl-4-oxocyclohex-2-en-1-yl)-3-methylpenta-2,4-dienoic acid (3'-methyl-(S)-abscisic acid) or a salt thereof to the peach tree.

* * * * *